(12) United States Patent
Coelingh Bennink et al.

(10) Patent No.: US 8,987,240 B2
(45) Date of Patent: *Mar. 24, 2015

(54) PHARMACEUTICAL COMPOSITIONS COMPRISING ESTETROL DERIVATIVES FOR USE IN CANCER THERAPY

(75) Inventors: Herman Jan Tijmen Coelingh Bennink, Driebergen (NL); Evert Johannes Bunschoten, Heesch (NL)

(73) Assignee: Pantarhei Bioscience B.V., Zeist (NL)

( * ) Notice: Subject to any disclaimer, the term of this patent is extended or adjusted under 35 U.S.C. 154(b) by 2246 days.

This patent is subject to a terminal disclaimer.

(21) Appl. No.: 10/532,320

(22) PCT Filed: Oct. 23, 2003

(86) PCT No.: PCT/NL03/00718
§ 371 (c)(1),
(2), (4) Date: Jun. 2, 2006

(87) PCT Pub. No.: WO2004/037269
PCT Pub. Date: May 6, 2004

(65) Prior Publication Data
US 2006/0247221 A1  Nov. 2, 2006

(30) Foreign Application Priority Data
Oct. 23, 2002 (EP) ................................. 02079414

(51) Int. Cl.
*A61K 31/565* (2006.01)

(52) U.S. Cl.
CPC .................................. *A61K 31/565* (2013.01)
USPC ........................................ 514/182; 514/171

(58) Field of Classification Search
USPC ................................................. 514/182, 171
See application file for complete search history.

(56) References Cited

U.S. PATENT DOCUMENTS

| | | |
|---|---|---|
| 3,440,320 A | 4/1969 | Sackler et al. |
| 3,797,494 A | 3/1974 | Zaffaroni |
| 4,460,372 A | 7/1984 | Campbell et al. |
| 4,573,996 A | 3/1986 | Kwiatek et al. |
| 4,624,665 A | 11/1986 | Nuwayser |
| 4,722,941 A | 2/1988 | Eckert et al. |
| 4,762,717 A | 8/1988 | Crowley, Jr. |
| 4,937,238 A | 6/1990 | Lemon |
| 5,063,507 A | 11/1991 | Lindsey et al. |
| 5,130,137 A | 7/1992 | Crowley, Jr. |
| 5,211,952 A | 5/1993 | Spicer et al. |
| 5,223,261 A | 6/1993 | Nelson et al. |
| 5,340,584 A | 8/1994 | Spicer et al. |
| 5,340,585 A | 8/1994 | Pike et al. |
| 5,340,586 A | 8/1994 | Pike et al. |
| 5,468,736 A | 11/1995 | Hodgen |
| 5,633,242 A | 5/1997 | Oettel et al. |

(Continued)

FOREIGN PATENT DOCUMENTS

| | | |
|---|---|---|
| DE | 2336433 A1 | 4/1975 |
| DE | 2336434 A1 | 4/1975 |

(Continued)

OTHER PUBLICATIONS

Definition of Prevent. [online]. Merriam-Webster Online Dictionary, 2006, [retrieved on Aug. 18, 2009]. Retrieved from the Internet: <URL:http://web.archive.org/web/20060518124943/http://merriam-webster.com/dictionary/prevent>, 1 page.*

(Continued)

*Primary Examiner* — John Pak
*Assistant Examiner* — Andriae M Holt
(74) *Attorney, Agent, or Firm* — Gilberto M. Villacorto; Sunit Talapatra; Foley & Lardner LLP

(57) ABSTRACT

The present invention relates to a method of treating or preventing estrogen-suppressed tumors in a mammal, said method comprising the administration of a therapeutically effective amount of an estrogenic component to said mammal, wherein the estrogenic component is selected from the group consisting of: substances represented by the following formula (I)

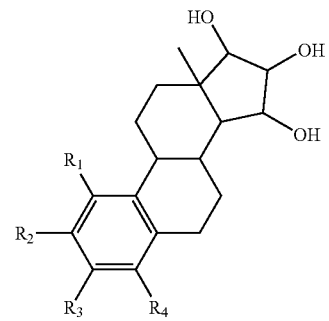

in which formula $R_1$, $R_2$, $R_3$, $R_4$, independently are a hydrogen atom, a hydroxyl group or an alkoxy group with 1-5 carbon atoms; precursors capable of liberating a substance according to the aforementioned formula when used in the present method; and mixtures of one or more of the aforementioned substances and/or precursors. The estrogenic component according to the invention is particularly useful in the treatment or prevention of colorectal and prostate cancer and, unlike commonly used estrogens, does not simultaneously enhance the risk of estrogen-stimulated cancers such as breast cancer.

6 Claims, 1 Drawing Sheet

(56) References Cited

U.S. PATENT DOCUMENTS

| | | | |
|---|---|---|---|
| 5,662,927 | A | 9/1997 | Ehrlich et al. |
| 5,827,843 | A | 10/1998 | Koninckx |
| 6,214,815 | B1 | 4/2001 | Shangold et al. |
| 6,291,456 | B1 | 9/2001 | Stein et al. |
| 6,500,814 | B1 | 12/2002 | Hesch |
| 8,048,869 | B2 * | 11/2011 | Bunschoten et al. ......... 514/171 |
| 2002/0013304 | A1 | 1/2002 | Wilson et al. |
| 2002/0156059 | A1 | 10/2002 | Elliesen |
| 2002/0183299 | A1 | 12/2002 | Voskuhl |
| 2003/0008012 | A1 | 1/2003 | Pena et al. |
| 2003/0203933 | A1 | 10/2003 | Lee et al. |
| 2004/0192598 | A1 | 9/2004 | Kragie |
| 2006/0247221 | A1 | 11/2006 | Bennink et al. |

FOREIGN PATENT DOCUMENTS

| | | | |
|---|---|---|---|
| DE | 2426779 | A1 | 12/1975 |
| EP | 0402950 | A | 12/1975 |
| EP | 468690 | A1 | 7/1991 |
| EP | 1 120 114 | A2 | 8/2001 |
| WO | 9603929 | A1 | 2/1966 |
| WO | 9218107 | A1 | 10/1992 |
| WO | WO 93/09771 | | 5/1993 |
| WO | WO 94/26207 | | 11/1994 |
| WO | 9502408 | A1 | 1/1995 |
| WO | WO 95/17895 | | 7/1995 |
| WO | 9603929 | A1 | 2/1996 |
| WO | 9858657 | A1 | 12/1998 |
| WO | WO 00/73416 | A1 | 12/2000 |
| WO | 0130357 | A | 5/2001 |
| WO | WO 01/32683 | A1 | 5/2001 |
| WO | 0185154 | A2 | 11/2001 |
| WO | WO 230355 | A2 * | 4/2002 |
| WO | 02094275 | A1 | 11/2002 |
| WO | 02094276 | A1 | 11/2002 |
| WO | 02094277 | A1 | 11/2002 |
| WO | 02094278 | A1 | 11/2002 |
| WO | 02094279 | A1 | 11/2002 |
| WO | 02094281 | A1 | 11/2002 |
| WO | 02094289 | A1 | 11/2002 |

OTHER PUBLICATIONS

Colon Cancer. Publication [online]. emedicinehealth (WebMD), 2011 [retrieved on Mar. 8, 2011]. Retrieved from the Internet: <URL:www.emedicinehealth.com/script/main/art.asp?articlekey=58782&pf=3&page=2> 10 pages.*

Estrogens in the Treatment of Advanced Prostate Cancer. [online]. Phoenix 5, CIHF, 1995, [retrieved on Mar. 13, 2011]. Retrieved from the Internet: <URL:http://www.phoenix5.org/Infolink/advanced/estrogen.html>, 2 pages.* al-Azzawi, F., Estrogen and Colon Cancer: Current Issues, Climacteric May 2002, PubMed, [retrieved from the Internet: <URL:http://www.ncbi.nlm.nih.gov/pubmed/11974557>, 1 page.*

Visser et al., "In vitro effects of estetrol on receptor binding, drug targets and human liver cell metabolism," CLIMACTERIC (2008) 11(1) Appx. II: 1-5.

Visser et al., "First human exposure to exogenous single-dose oral estetrol in early postmenopausal women," CLIMACTERIC (2008) 11(1): 1-10.

Visser et al., "Clinical applications of estetrol," J. of Steroid Biochem and Molecular Biol. (2009) 114: 85-89.

Sitruk-Ware et al., "Local Hormonal Treatment for Urogenital Atrophy After Menopause", Shweiz. Rundsch. Med. Praxis, 1997, pp. 1245-1248, vol. 86, No. 33.

Schmidt et al., "Treatment of Skin Aging with Topical Estrogens", Int. J. Dermatol., 1996, pp. 669-674, vol. 35, No. 9.

Sitruk-Ware, English Translation, 1997. Praxis, Schweizerische Rundschau fur Medizin, vol. 86, No. 33, pp. 1-13.

Younglai et al., Journal of Clinical Endocrinology and Metabolism, 1968, vol. 28, Issue 11, pp. 1611-1617.

Webster Ninth New Collegiate Dictionary, 2000, Definition of Prevention, p. 1.

Willhite et al., Pharmacotherapy, 2001, vol. 21, Issue 4, pp. 464-480.

Fishman et al., "Fate of 15 α-Hydroxyestriol-3H in Adult Man", J. Clin. Endocrinol. Metab., (1970), vol. 31, pp. 436-438.

Seeger et al., "The inhibitory effect of endogenous estrogen metabolies on copper-mediated in vitro oxidation of LDL", Int. Journal of Clinical Pharmacology and Therapeutics, (1998), vol. 36, No. 7, pp. 383-385.

Katzung, Basic and Clinical Pharmacology, 6th ed., 1995, pp. 608-624.

Schwartz, "A Model for the Regulation of Ovulation in the Rat", Recent Prog. Horm. Res., vol. 25, pp. 1-55, (1969).

Beattie et al., "The Differential Effects of Diestrous Progestogen Administration on Proestrous Gonadotrophin Levels, Endocrinol", vol. 97, pp. 885-890, (1975).

De Visser et al., Endocrinological Studies with (7a, 17 a)-17-Hydroxy-7-me norpregn-5(10)-en-20-yn-3-one (Org OD 14), Arzneim, Forsh., vol. 34, pp. 1010-1020, (1984).

National Cancer Institute: Breast cancer prevention retrieved online Aug. 7, 2007 from the internet; http://www.cancer.gov/templates/doc.aspx?viewed+D972A74B-D25A-4F86-B8ED-33EB3C0450E4&version, p. 1.

Medline Plus: Medical Encyclopedia: Ovarian cancer retrieved online on Aug. 9, 2007 from the internet: https://www.nlm.nih.gov/medlineplus/ovariancancer.html, p. 1 dated Jul. 31, 2007.

National Institute of Child Health and Human Development, NIH Publication No. 02-2413 retrieved online on Aug. 9, 2007.

Breast Cancer Prevention retrieved online Aug. 7, 2007 from the internet; http://www.cancer.gov/cancertopics/pdq/prevention/breast/Patient/page 3.

Prophylactic definition—Medical Dictionary of Popular Medical Terms; retrieved on Mar. 14, 2008 via www.medterms.com/script/main/art.asp?articlekey+11902.

Zips et al., in vivo, 2005, vol. 19, pp. 1-8.

Holinka et al., Biology of Reproduction, 1980, vol. 22, pp. 913-926.

Martucci et al., "Impact of Continuously Administered Catechol Estrogens on Uterine Growth and Luteinizing Hormone Secretion", Endocrinology (Dec. 1979), vol. 105, No. 6, pp. 1288-1292.

Weigert et al., "Comparison of Stimulation with Clomiphenes Citrate in Combination with Recombinant Follicle Stimulating Hormone and Recombinant Luteinizing Hormone to Stimulation with a Gonadotropin-Releasing Hormone Agonist Protocol: A Prospective Randomized Study", Fertility and Sterility, (Jul. 2002), vol. 78, No. 1, pp. 34-39.

Trotter et al., "Effects of Postnatal Estradiol and Progesterone Replacement in Extremely Preterm Infants", J. Clin. Endocrinol Metab., (Dec. 1999), vol. 84, No. 12, pp. 4531-4535.

Office Action mailed on May 16, 2008 in U.S. Appl. No. 10/478,357.
Office Action mailed on Dec. 16, 2008 in U.S. Appl. No. 10/478,357.
Office Action mailed on May 28, 2009 in U.S. Appl. No. 10/478,357.
Office Action mailed on Nov. 2, 2009 in U.S. Appl. No. 10/478,357.
Office Action mailed on Apr. 6, 2007 in U.S. Appl. No. 10/478,365.
Office Action mailed on Sep. 7, 2007 in U.S. Appl. No. 10/478,365.
Office Action mailed on Apr. 1, 2008 in U.S. Appl. No. 10/478,365.
Office Action mailed on Jun. 8, 2009 in U.S. Appl. No. 10/478,365.
Office Action mailed on Jan. 24, 2007 in U.S. Appl. No. 10/495,707.
Office Action mailed on Dec. 28, 2007 in U.S. Appl. No. 10/495,707.
Office Action mailed on Aug. 19, 2008 in U.S. Appl. No. 10/495,707.
Office Action mailed on May 22, 2009 in U.S. Appl. No. 10/495,707.
Office Action mailed on Oct. 15, 2007 in U.S. Appl. No. 10/517,509.
Office Action mailed on Dec. 19, 2007 in U.S. Appl. No. 10/517,509.
Office Action mailed on Mar. 26, 2008 in U.S. Appl. No. 10/517,509.
Office Action mailed on Jan. 5, 2009 in U.S. Appl. No. 10/517,509.
Office Action mailed on Aug. 18, 2009 in U.S. Appl. No. 10/517,509.
Office Action mailed on Dec. 7, 2009 in U.S. Appl. No. 10/517,509.
Office Action mailed on Apr. 3, 2007 in U.S. Appl. No. 10/517,686.
Office Action mailed on Aug. 9, 2007 in U.S. Appl. No. 10/517,686.
Office Action mailed on Apr. 4, 2008 in U.S. Appl. No. 10/517,686.
Office Action mailed on May 29, 2009 in U.S. Appl. No. 10/517,686.
Office Action mailed on Apr. 23, 2007 in U.S. Appl. No. 10/521,040.
Office Action mailed on Aug. 17, 2007 in U.S. Appl. No. 10/521,040.
Office Action mailed on Apr. 2, 2008 in U.S. Appl. No. 10/521,040.

(56) References Cited

OTHER PUBLICATIONS

Office Action mailed on Jun. 1, 2009 in U.S. Appl. No. 10/521,040.
Allen et al., The Induction of a Sexually Mature Condition in Immature Females by Injection of the Ovarian Follicular Hormone, Washington University School of Medicine, Saint Louis, The Department of Anatomy, University of Missouri, and The Laboratories of Biological Chemistry, Saint Louis University School of Medicine, May 16, 1924, pp. 577-587.
Jones, M.S. et al., The Effects of Various Steroids on the Vaginal Histology in the Rat, Fertility and Sterility, Apr. 1973, pp. 284-291, vol. 24, No. 4.
Reel et al., Survey and Assessment of Mammalian Estrogen Biological Assays for Hazard Characterization, Fundamental and Applied Toxicology, 1996, pp. 288-305, vol. 34.
Kuipers et al., Enterohepatic Circulation in the Rat, Gastroenterology, 1985, pp. 403-411, vol. 88.
Avvakumov et al., Steroid-binding Specificity of Human Sex Hormone-binding Globulin Is Influenced by Occupancy of a Zinc-binding Site, The Journal of Biological Chemistry, 2000, pp. 25920-25925, vol. 275, No. 34.
Elger et al., Sulfamates of Various Estrogens are Prodrugs with Increased Systemic and Reduced Hepatic Estrogenicity at Oral Application, J. Steroid Biochem. Molec. Biol., 1995, pp. 395-403, vol. 55, No. 3/4.
Hammond et al., A versatile method for the determination of serum cortisol binding globulin and sex hormone binding globulin binding capacities, Clinics Chimica Acta, 1983, pp. 101-110, vol. 132.
Mueck et al., Angiogenetic and Anti-Angiogenetic Effects of Estradiol and its Metabolites, J. Clin. Basic Cardiol., 2001, pp. 153-156, vol. 4.
Lippert et al., The effects of A-ring and D-ring metabolites of estradiol on the proliferation of vascular endothelial cells, Life Sciences, 2000, pp. 1653-1658, vol. 67.
Coffey et al., Similarities of Prostate and Breast Cancer: Evolution, Diet, and Estrogens, XP-001027445, Elsevier Science, Inc., 2001.
Mobbs et al., Suppression of the Growth of the Androgen-Insensitive R3327 Hi Rat Prostatic Carcinoma by Combined Estrogen and Antiprogestin Treatment, Steroid Biochem. Molec. Biol., 1991, pp. 713-722, vol. 39, No. 5A.
Martucci et al., Uterine Estrogen Receptor Binding of Catecholestrogens and of Estetrol (1, 3, 5(10)—Estratriene-3, 15α, 16α, 17 β-Tetrol), Institute for Steroid Research and Department of Oncology and Biochemistry, Montefiore Hospital and Medical Center, Albert Einstein College of Medicine, Bronx, NY, Nov. 8, 1975, pp. 325-333, vol. 27, No. 3.
Tseng et al., Competition of Estetrol and Ethynylestradiol With Estradiol for Nuclear Binding in Human Endometrium, Journal of Steroid Biochemistry, 1976, pp. 817-822, vol. 7.
Holinka et al., In vivo Effects of Estetrol on the Immature Rat Uterus, Biology of Reproduction, 1979, pp. 242-246, vol. 20.
Holinka et al., Comparison of Effects of Estetrol and Tamoxifen with Those of Estriol and Estradiol on the Immature Rat Uterus, Biology of Reproduction, 1980, pp. 913-926, vol. 22.
Lopez-Otin et al., Breast and Prostate Cancer: An Analysis of Common Epidemiological, Genetic, and Biochemical Features, Endocrine Reviews, Aug. 1998, pp. 365-396, vol. 19, No. 4.
Kuhnel et al., Androgen Dependency of Human Ovarian Cancer May Be Due to a Para or Autocrine Action, XP-009025474, Abstracts of the First International Conference of Anticancer Research, Oct. 26-30, 1985, p. 603.
Raj et al., Pineal-Thyroid Relationship in Breast Cancer, XP-009025474, Abstracts of the First International Conference of Anticancer Research, Oct. 26-30, 1985, p. 603.
Alvarado-Pisani et al., Thyroid Hormone Receptors in Human Breast Cancer: Effect of the Thyroxine Administration and Interrelation With Sex Hormone Axis, XP-009025474, Abstracts of the First International Conference of Anticancer Research, Oct. 26-30, 1985, p. 603.
Corbishley et al., Androgen Receptor in Human Normal and Malignant Pancreas and Cell Lines, XP-009025474, Abstracts of the First International Conference of Anticancer Research, Oct. 26-30, 1985, p. 603.
Heining, et al. "Clinical management of breast cancer in males: a report of four cases", European Journal of Obstetrics & Gynecology and Reproductive Biology, 2002, vol. 10, pp. 67-73.
Malkowicz, "The role of Diethylstilbestrol in the Treatment of Prostate Cancer", Urology, 2001, vol. 58, Supplement 2A, Aug. 2001, pp. 108-113.
Holinka et al., "Estetrol: A unique steroid in human pregnancy," J. of Steroid Biochem and Molecular Biol. (2009) 110: 138-143.
Coelingh Bennink et al., "Oral bioavailability and bone sparing effects of estetrol in an osteoporosis model," CLIMACTERIC (2008) 11 (Supp 3): 1-13.
Albertazzi Paola et al., "The Effect of Tibolone Versus Continuous Combined Norethisterone Acetate and Oestradiol on Memory, Libido and Mood of Postmenopausal Women: A Pilot study"; Database Biosis 'Onlinel; Oct. 31, 2000; pp. 223-229; vol. 36, No. 3; Biosciences Information Service, Philadelphia, PA., U.S.
Jansson et al., "Estrogen Induces a Potent Suppression of Experimental Autoimmune Encephalomyelitis and Collagen-Induced Arthritis in Mice", Journal of Neuroimmunology, Elsevier Science Publishers BV XX, 1994, vol. 53, No. 2, pp. 203-207.
Erdbruegger et al., Drug Discovery Today: Disease Mechanisms (2004), vol. 1, pp. 73-81.
Lab Tests Online (www.labtestsonline.org/understanding/conditions/autoimmune.html) retrieved on Aug. 3, 2007.
www.tiscali.co.uk/lifestyle/healthfitness/health_advice/netdoctor/archive/000489.html, Aug. 27, 2009.
MedlinePlus Medical Encyclopedia: Mutiple Sclerosis, retrieved on Mar. 28, 2008 via www.nlm.nih.gov/medlineplus/ency/article/000737.htm, dated on Aug. 6, 2007, p. 1 and 2.
MedlinePlus Medical Encyclopedia: Multiple Sclerosis, retrieved on Mar. 28, 2008, p. 2; also see WebMD: Multiple Sclerosis—Prevention, retrieved on Mar. 28, 2008 via www.webmd.com/multiple-sclerosis/tc/multiple-sclerosis-ms-prevention, dated on Mar. 23, 2006.
MedlinePlus Medical Encyclopedia: rheumatoid arthritis, retrieved on Mar. 28, 2008 via www.nlm.nih.gov/medlineplus/ency/article/000431.htm, dated on Jul. 27, 2007, p. 1-2 and 4; also WebMD: Rheumatoid Arthritis—Prevention, retrieved on Mar. 28, 2008 via www.webmd.com/rheumatoid-arthritis/tc/rheumatoid-arthritis-prevention, dated on Aug, 23, 2006.
Shah et al., "Estrogen and Skin. An Overview", Am. J. Clin. Dermatol., 2001, pp. 143-150, vol. 2, No. 3.
Shanklin et al., "Aqueous Estrogens in the Management of Respiratory Distress SYndrome", J. Reprod. Med. (Aug. 1970), vol. 5, No. 2, pp. 53-71.
Chemical Abstracts Service, Columbus Ohio, US: Jakowicki, "Evaluation of Estriol Level in the Amniotic Fluid in Prolonged Pregnancy", XP002458625, 1979.
Gorwill et al., "Unconjugated Serum Oestriol Levels in Mother and Baby with Meconium Staining of the Amniotic Fluid", Br. J. Obstet. Gynaecol. (Aug. 1978), vol. 85, No. 8, pp. 602-604.
Fogary, Jr., "Postmaturity", J. Am. Osteopath. Assoc., (Jan. 1976), vol. 75, No. 5, pp. 512-517.
Office Action mailed on Jan. 11, 2008 in U.S. Appl. No. 10/478,262.
Office Action mailed on May 15, 2008 in U.S. Appl. No. 10/478,262.
Office Action mailed on Feb. 19, 2009 in U.S. Appl. No. 10/478,262.
Office Action mailed on Jun. 9, 2009 in U.S. Appl. No. 10/478,262.
Office Action mailed on Nov. 18, 2008 in U.S. Appl. No. 10/478,264.
Office Action mailed on May 22, 2009 in U.S. Appl. No. 10/478,264.
Office Action mailed on Mar. 17, 2008 in U.S. Appl. No. 10/478,357.
Cushing et al., Risk of Endometrial Cancer in Relation to Use of Low-Dose, Unopposed Estrogens, Estrogen and Endometrial Cancer, Jan. 1998, pp. 35-39, vol. 91, No. 1.
Tavani et al., The Adverse Effects of Hormone Replacement Therapy, Drugs & Aging, May 14, 1999, pp. 347-357, vol. 5.
Pike et al., Progestins and menopause: epidemiological studies of risks of endometrial and breast cancer, Steroids, 2000, pp. 659-664, vol. 65.

(56) References Cited

OTHER PUBLICATIONS

Beral et al., Use of HRT and the subsequent risk of cancer, Journal of Epidemiology and Biostatisitics, 1999, pp. 191-215, vol. 4, No. 3.

Tulchinsky et al., Plasma Estetrol as an Index of Fetal Well-being, JCE & M, 1075, pp. 560-567, vol. 40, No. 4.

Levine, et al., Uterine vascular effects of estetrol in nonpregnant ewes, Am. J. Obstet. Gynecol., Mar. 15, 1984, pp. 735-738.

Jozan et al., Different effects of oestradiol, oestriol, oestrol and of oestrone on human breast cancer cells, Acta Endocrinologica, 1981, pp. 73-80.

Tseng et al., Heterogeneity of Saturable Estradiol Binding Sites in Nuclei of Human Endometrium Estetrol Studies, Departments of Obstetrics and Gynecology, State University of New York at Stony Brook, Stony Brook, NY, USA and Mount Sinai School of Medicine, New York, NY, Mar. 1978, pp. 1145-1148.

Martucci et al., Direction of Estradiol Metabolism as a Control of its Hormonal Action—Uterotrophic Activity of Estradiol Metabolites, Institute for Steroid Research, Mentefiore Hospital and Medical Center, and Department of Biochemistry, Albert Einstein College of Medicine, Bronx, New York, May 13, 1977, pp. 1709-1714.

Murphy et al., Endometrial effects of long-term low-dose administration of RU486, Fertility and Sterility, Apr. 1995, pp. 761-766, vol. 63, No. 4.

Allen et al., An Ovarian Hormone Preliminary Report on Its Localization, Extraction and Partial Purification and Action in Test Animals, Jour. A. M. A., Sep. 8, 1923, pp. 819-821, vol. 81, No. 10.

* cited by examiner

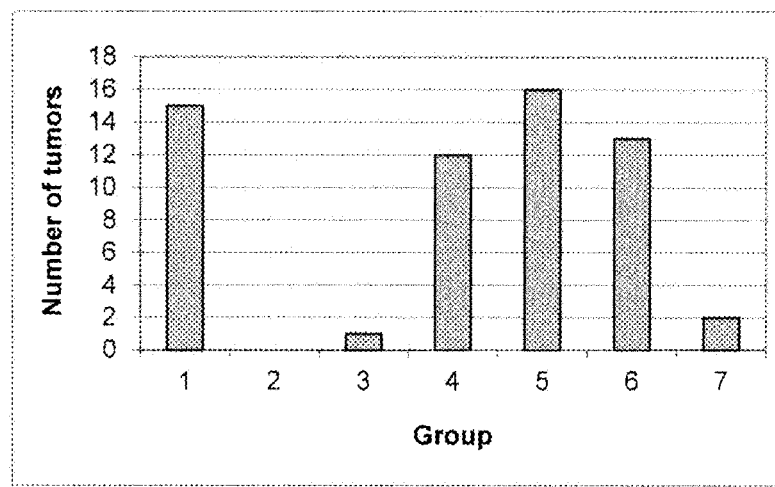

PHARMACEUTICAL COMPOSITIONS COMPRISING ESTETROL DERIVATIVES FOR USE IN CANCER THERAPY

TECHNICAL FIELD OF THE INVENTION

The present invention relates to a method for treating or preventing estrogen-suppressed tumours in a mammal by administering an effective amount of a special estrogenic component to said mammal. The present method is particularly suitable for treating or preventing colorectal and prostate cancer.

BACKGROUND OF THE INVENTION

Colorectal carcinoma is a malignant neoplastic disease. There is a high incidence of colorectal carcinoma in the Western world. Tumours of this type often metastasize through lymphatic and vascular channels. Many patients with colorectal carcinoma eventually die from this disease. To date, systemic therapies and chemotherapies have been developed for the treatment of colorectal cancer. However, no therapies have exhibited sufficient anti-tumour activity to prolong the survival of colorectal carcinoma patients with metastatic disease with any degree of reliability. As a result, a need still exists to develop methods for the successful treatment or prevention of colorectal carcinoma.

In an article by Al-Azzawi et al. ("Estrogen and colon cancer: current issues", Climacteric 2002; 5:3-14) current epidemiological data on the incidence and mortality of colon cancer in post-menopausal women using hormone replacement therapy is reviewed. Hormone replacement therapy (HRT) comprises the administration of estrogen to prevent or treat symptoms resulting from estrogen deficiency (hypoestrogenism). The authors conclude that estrogen use confers overall protection, with a reduction in the incidence of colon adenoma and carcinoma of about 30%. It is said that estrogen use reduces the colon cancer-related mortality.

U.S. Pat. No. 6,291,456 (Signal Pharmaceuticals Inc.) relates to compounds that modulate gene expression through the estrogen receptor as well as to methods for treating a large number of estrogen-related conditions, including colon cancer. The compounds according to this US-patent include both estrogen antagonists and agonists. It is observed in the patent that those compounds that are estrogen antagonists are useful as antiestrogens in, for example, breast and ovarian tissue and thus are useful in the treatment and prevention of breast and ovarian cancer. Those compounds that are estrogen agonists are recommended for other therapeutic and prophylactic uses.

As will be evident from the above publications, it has been suggested in the prior art that the administration of estrogens to postmenopausal females may help to reduce the risk of colon cancer. However, this observation does not automatically warrant the conclusion that it would be advisable to treat or prevent estrogen-suppressed cancers, such as colon cancer, by administering estrogen. Indeed, it is well known that estrogens increase the risk of "estrogen-stimulated cancers", e.g. endometrial cancer in females (Cushing et al., 1998. Obstet. Gynecol. 91, 35-39; Tavani et al., 1999. Drugs Aging, 14, 347-357) and breast cancer in both females and males (Tavani et al., 1999. Drugs Aging, 14, 347-357; Pike et al., 2000. Steroids, 65, 659-664, Heinig et al. 2002, European Journal of Obstetrics & Gynecology, 102, 67-73), by inducing an estrogen receptor mediated increase in the frequency of cell division (proliferation) within these tissues. Cell division is essential in the complex process of genesis of human cancer since it per se increases the risk of genetic error, particularly genetic errors such as inactivation of tumour suppressor genes.

Since the incidence of the aforementioned estrogen-stimulated cancers in industrialised countries is very high, the administration of estrogens in the treatment or prevention of e.g. colon cancer is associated with very significant drawbacks. Thus, there is a requirement for an estrogen that could be employed in the treatment of estrogen-suppressed tumours without enhancing the risk of estrogen-stimulated tumours.

Prostate cancer is the second leading cause of cancer mortality in men in the USA. For the past six decades, hormonal therapy has been an important treatment of advanced prostate cancer. One such method employs diethylstilbestrol (DES) to suppress endogenous androgen production. DES is a substance that is known to exhibit estrogenic activity. However, the use of DES is marred by significant cardiovascular toxicity. Strategies to reduce thromboembolic events, such as dose reduction or the use of warfarin sodium were unsuccessful (Malkwicz et al., "The role of diethylstilbestrol in the treatment of prostate cancer", Urology 2001 August; 58(2 Suppl 1):108-13). In addition, the application of DES is believed to enhance the risk of breast cancer.

Consequently, there is a need for an estrogenic substance that may be used in the treatment or prevention of estrogen-suppressed tumours, such as colorectal tumours or prostate tumours, and which does not impose a risk factor for the development of estrogen-stimulated cancers or display significant cardiovascular toxicity.

SUMMARY OF THE INVENTION

The inventors have unexpectedly found that the aforementioned requirements are met by estrogenic substances that are represented by the following formula

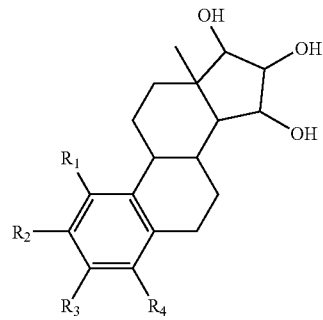

in which formula $R_1$, $R_2$, $R_3$, $R_4$ independently are a hydrogen atom, a hydroxyl group or an alkoxy group with 1-5 carbon atoms.

A known representative of this group of estrogenic substances is 1,3,5 (10)-estratrien-3,15α,16α,17β-tetrol, also known by the names of estetrol, oestetrol and 15a-hydroxyestriol. Estetrol is an estrogen that is produced by the fetal liver during human pregnancy. Unconjugated estetrol levels in maternal plasma peak at about 1.2 ng/ml at term pregnancy and are about 12 times higher in fetal than in maternal plasma (Tulchinsky et al., 1975. J. Clin. Endocrinol. Metab., 40, 560-567).

U.S. Pat. No. 5,340,585 and U.S. Pat. No. 5,340,584 describe compositions and methods for treating benign gynaecological disorders, such as premenstrual syndrome, comprising the combined administration of a GnRH composition and an estrogenic composition. U.S. Pat. No. 5,340,585 furthermore mentioned the use of such a method for reducing the risk of cancers of the breast and the ovary. The latter cancers are generally regarded as estrogen sensitive cancers, i.e. cancers whose formation and growth is stimulated by estrogens, other than the estrogenic components according to the present invention, especially estrogens selected from the group consisting of 17β-estradiol, ethinyl estradiol, as well as precursors and metabolites thereof.

It is very surprising that the present estrogenic substances do not enhance the risk of estrogen-stimulated tumours as the skilled person would expect estrogenic substances to enhance the formation and growth of such tumours. Since the present estrogenic substances do not appear to exhibit estrogen antagonistic properties, this finding is truly unexpected.

The present estrogenic substances were found to exhibit a relatively high affinity for the ERa receptor, or conversely a relatively low affinity for the ERβ receptor. It is believed that this receptor specificity is somehow associated with the observation that the present substances, unlike commonly used estrogens, do not stimulate proliferation in estrogen-stimulated tissues. However, the mechanisms that govern the ER signalling pathways that are responsible for this phenomenon are as yet poorly understood, despite the considerable scientific effort that is ongoing in this area.

It is known that most estrogens bind to both ERs which, in the presence of tissue-specific co-activators and/or co-repressors, bind to an estrogen response element in the regulatory region of genes or to other transcription factors. Given the complexity of ER signalling, along with the tissue-specific expression of ERa and ERβ and its co-factors, it is now recognised that ER ligands can act as estrogen agonists or even as estrogen antagonists in a tissue-specific manner.

It is also now known that estrogen modulates cellular pharmacology through gene expression, and that the estrogen effect is mediated by the estrogen receptors. The effect of the estrogen receptor on gene regulation can be mediated by a direct binding of ER to the estrogen response element, binding of ER to other transcription factors such as NF-?B, C/EBPβ and through non-genomic effects involving ion channel receptors. Progress over the last few years has shown that ER associates with co-activators (e.g., SRC-1, CBP and SRA) and co-repressors (e.g., SMRT and N-CoR), which also modulate the transcriptional activity of ER in a tissue-specific and ligand-specific manner. In addition, evidence now suggests that the majority of estrogen-regulated genes do not have a classical estrogen response element. In such cases, ER interacts with the transcription factors critical for regulation of these genes. Transcription factors known to be modulated in their activity by ER include, for example, AP-1, NF-?B, C/EBP and Sp-1.

Given the complexity of ER signalling, as well as the various types of tissue that express ER and its co-factors, it is commonly believed that ER ligands can no longer simply be classified as either pure antagonists or agonists. This view is supported by the findings of Paech et al. (Science 277, 1508-1510, 1997) who have reported that 17β-estradiol activates an AP-1 site in the presence of ERa, but inhibits the same site in the presence of ERβ. In contrast, the ER ligands raloxifene (Eli Lilly & Co.) and tamoxifen and ICI-182,780 (Zeneca Pharmaceuticals) stimulate the AP-1 site through ERβ, but inhibit this site in the presence of ERa.

ERa and ERβ are known to have both overlapping and different tissue distributions, as analysed predominantly by RT-PCR or in-situ hybridisation. Very often tissues express both ERa and ERβ, but the receptors are localised in different cell types.

In summary, although the mechanisms by which the present estrogenic component exerts its favourable effect are as yet unknown, it is evident that said estrogenic component is different from estrogenic substances, such as 17β-estradiol and ethinyl estradiol, in that it exhibits a relatively high affinity for the ERa receptor in comparison to the ERβ receptor. It will also be clear from the above that this specificity may well be responsible for the efficacy of the present estrogenic component in the treatment or prevention of estrogen-suppressed tumours without the disadvantage of enhancing the risk of estrogen-stimulated tumours in both females and males.

BRIEF DESCRIPTION OF TILE DRAWINGS

FIG. 1 shows the number of tumours per the following treatment groups (n=12): Group 1 oral treatment with 3.0 ml/kg/day vehicle; Group 2 surgically castrated animals receiving placebo treatment with 3.0 ml/kg/day vehicle; Group 3 tamoxifen 3 mg/kg/day orally; Group 4 ethinylestradiol (RE) 0.025 mg/kg/day orally; Group 5 ER 0.125 mg/kg/day orally; Group 6 estetrol (E4) 0.5 mg/kg/day orally; Group 7 EE 2.5 mg/kg/day orally.

DETAILED DESCRIPTION OF THE INVENTION

Accordingly, the present invention relates to a method of treating or preventing estrogen-suppressed tumours in a mammal, said method comprising the administration of a therapeutically effective amount of an estrogenic component to said mammal, wherein the estrogenic component is selected from the group consisting of: substances represented by the following formula

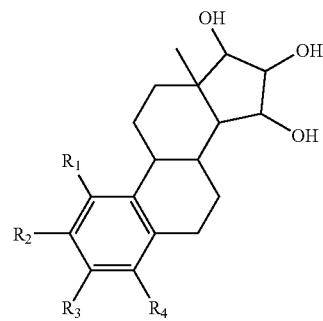

in which formula $R_1$, $R_2$, $R_3$, $R_4$ independently are a hydrogen atom, a hydroxyl group
or an alkoxy group with 1-5 carbon atoms;
precursors capable of liberating a substance according to the aforementioned formula when used in the present method; and mixtures of one or more of the aforementioned substances and/or precursors.

As used herein the term "tumour" refers to a new growth of tissue in which the multiplication of cells is uncontrolled and progressive. The term tumour encompasses both malignant and benign tumours.

The term "estrogen-suppressed tumour" refers to a tumour whose formation and growth is suppressed by the administration of estrogens and is not restricted to tumours whose formation and growth are directly affected by estrogens. For instance, estrogen-suppressed tumours also encompasses tumours whose formation and growth are stimulated by androgens and whose formation and growth may be suppressed by administration of estrogen in an amount effective to inhibit endogenous production of androgens. Examples of such androgen-stimulated tumours that are to be regarded as estrogen-suppressed tumours include prostate tumours and prostate hypertrophy.

The term "estrogen-stimulated tumour" refers to a tumour whose formation and growth is stimulated by (endogenous or exogenous) estrogens, other than the estrogenic components according to the present invention, especially estrogens selected from the group consisting of 17β-estradiol, conjugated equine estrogens, ethinyl estradiol, as well as precursors and metabolites thereof.

The term "cancer" refers to cells that have undergone a malignant transformation that makes them pathological to the host organism.

The present estrogen substances are distinct from both the biogenic and synthetic estrogens that are commonly applied in pharmaceutical formulations in that the 5 membered ring in the steroid skeleton comprises 3 hydroxyl substituents rather than 0-2. In a particularly preferred embodiment at least one of $R_1$, $R_2$, $R_3$ and $R_4$ represents a hydroxyl group, meaning that the estrogen substance contains at least 4 hydroxyl groups. Preferably, the estrogenic component applied as the active component in the present composition is a so called biogenic estrogen, i.e. an estrogen that occurs naturally in the human body, a precursor of a biogenic estrogen or a mixture thereof. Because biogenic estrogens are naturally present in the fetal and female body, side-effects are not expected to occur, particularly not if the serum levels resulting from the exogenous administration of such estrogens do not substantially exceed naturally occurring concentrations.

In a preferred embodiment of the present invention the estrogen substance contains 4 hydroxyl groups. In another preferred embodiment, no more than 3 of $R_1$, $R_2$, $R_3$, $R_4$ are hydrogen atoms. Also, in the aforementioned formula, $R_1$ preferably represents a hydrogen atom. In said formula preferably at least 2, more preferably at least 3 of the groups $R_1$, $R_2$, $R_3$ and $R_4$ represent a hydrogen atom.

The estrogenic substances according to the formula encompass various enantiomers since the carbon atoms that carry hydroxyl-substituents are chirally active. In one preferred embodiment, the present estrogen substance is 15a-hydroxy substituted. In another preferred embodiment the substance is 16a-hydroxy substituted. In yet another preferred embodiment, the substance is 17β-hydroxy substituted. Most preferably the estrogenic substances are 15α,16α,17β-trihydroxy substituted. The other chirally active carbon atoms in the steroid skeleton of the present estrogenic components preferably have the same configuration as the corresponding carbon atoms in 17β-estradiol and other biogenic estrogens.

In a preferred embodiment of the present invention $R_3$ represents a hydroxyl group or an alkoxy group. In another preferred embodiment the groups $R_1$, $R_2$ and $R_4$ represent hydrogen atoms, in which case the substance is 1,3,5 (10)-estratrien-3,15,16,17-tetrol. A preferred isomer of the latter substance is 1,3,5 (10)-estratrien-3,15α,16α,17β-tetrol (es-tetrol).

The invention also encompasses the use of precursors of the estrogen substances that constitute the active component in the present method. These precursors are capable of liberating the aforementioned estrogen substances when used in the present method, e.g. as a result of metabolic conversion. These precursors are preferably selected from the group of derivatives of the present estrogen substances, wherein the hydrogen atom of at least one of the hydroxyl groups has been substituted by an acyl radical of a hydrocarbon carboxylic, sulfonic acid or sulfamic acid of 1-25 carbon atoms; tetrahydrofuranyl; tetrahydropyranyl; or a straight or branched chain glycosydic residue containing 1-20 glycosidic units per residue. Typical examples of precursors which can suitably be used in accordance with the invention are esters that can be obtained by reacting the hydroxyl groups of the estrogen substances with substances that contain one or more carboxy ($M^{+-}OOC$—) groups, wherein $M^+$ represents a hydrogen or (akali)metal cation. Hence, in a particularly preferred embodiment, the precursors are derivatives of the estrogen substances, wherein the hydrogen atom of at least one of the hydroxyl groups in said formula has been substituted by —CO—R, wherein R is a hydrocarbon radical comprising from 1-25 carbon atoms. Preferably R is hydrogen, or an alkyl, alkenyl or aryl radical comprising from 1-20 carbon atoms.

The method according to the present invention may suitably be used to treat mammals such as cattle, pets and particularly humans. The method may be used to treat both females and males, be it that it is most beneficial when used in females. The method may be applied advantageously in pre-menopausal, perimenopausal and postmenopausal females.

The present method is particularly effective when the administration is continued for a prolonged period of time. Usually, the method comprises the uninterrupted administration of the estrogenic component during a period of at least 5 days. Preferably the uninterrupted administration is continued for at least 30 days, more preferably for at least 90 days.

The present method may suitably employ enteral or parenteral administration of the estrogenic component. The term "parenteral administration" as used in here encompasses transdermal, intravenous, intranasal, intravaginal, pulmonary, buccal, subcutaneous, intramuscular and intra-uterine administration. The term "enteral administration" includes oral as well as rectal administration.

Preferably the mode of administration is selected from the group consisting of oral, transdermal, intravenous, intranasal, intravaginal, pulmonary, rectal, buccal, subcutaneous, intramuscular or intra-uterine administration. More preferably the mode of administration is selected from the group consisting of oral, transdermal, intravenous, subcutaneous, intranasal, pulmonary and vaginal administration. In a particularly preferred embodiment the present method employs oral, transdermal, intranasal or subcutaneous administration. Even more preferably the present method employs oral or transdermal administration.

Oral, intravenous, subcutaneous, intramuscular, intranasal, rectal, buccal and pulmonary administration are ideally suited for (at least) once daily administration. Transdermal and intravaginal administration are advantageously applied at frequencies between once a day and once a month. Intra-uterine administrations is advantageously operated at administration frequencies between once weekly and once monthly. Subcutaneous and intramuscular administration may also suitably be done in the form of depot injections at intervals of 1 week to 6 months, preferably at intervals of 4 weeks to 3 months.

For reasons of convenience, the present method preferably utilises administration intervals of 1 day, 1 week or 1 month. Regimens that employ once daily oral, subcutaneous, intravenous or intranasal administration, once weekly transdermal or once monthly intravaginal or subcutaneous administration are particularly preferred.

Irrespective of the mode of administration, the estrogenic component is preferably administered in an amount effective to achieve a blood serum concentration of at least 1 nanogram per liter, more preferably of at least 10 nanogram per liter, most preferably at least 100 nanogram per liter. Generally the resulting blood serum concentration of the estrogenic component will not exceed 100 μg per liter, preferably it will not exceed 50 μg per liter, more preferably it will not exceed 25 μg per liter.

In accordance with the present method the estrogenic component is usually administered in an amount of less than 1 mg per kg of bodyweight per day, preferably of less than 0.4 mg per kg of bodyweight per day. In order to achieve a significant impact from the administration of the estrogenic component, it is advisable to administer in an amount of at least 1 μg per kg of bodyweight per day. Preferably, the administered amount is at least 5 μg per kg of bodyweight per day.

Oral administration of the active component is preferably done in an amount of less than 400 μg per kg of bodyweight per day, preferably of less than 200 μg per kg of bodyweight per day. In order to achieve a significant impact from the administration of the active component, it is advisable to orally administer in an amount of at least 2 μg per kg of bodyweight per day. Preferably, the orally administered amount is at least 5 μg per kg of bodyweight per day. In the present method, particularly when used in humans, the estrogenic component is usually administered in an average dosage of at least 0.05 mg per day, preferably of at least 0.1 mg per day. The maximum dosage is normally kept below 40 mg per day, preferably below 20 mg per day.

The present method of treatment comprises administering to a mammal in need of such a therapy an effective amount of the estrogenic component. The amount needed to be effective will differ from individual to individual and are determined by factors such as the individual's gender, body weight, route of administration and the efficacy of the particular estrogenic component used.

In the present method, particularly when used in humans, the estrogenic component is usually administered orally in an average dosage of between 0.01 and 20 mg per day, preferably of between 0.05 and 10 mg per day. Similarly, the parenteral dosage preferably is at least 0.05, preferably at least 0.1 mg per day. The average maximum parenteral dosage is normally kept below 40 mg per day, preferably below 20 mg per day.

In a particularly preferred embodiment of the invention the method employs oral administration of the active estrogenic component. The term oral administration as used in here also encompasses oral gavage administration. The inventors have found that, despite its low potency, estetrol and related estrogenic substances may advantageously be administered orally. Although the inventors do not wish to be bound by theory, it is believed that the efficacy of orally administered estetrol-like substances results from the combination of special pharmacokinetic (ADME) and pharmacodynamic properties of these substances.

The inventors have discovered that the oral bioavailability of estetrol-like substances is exceptionally high and that their in vivo half-life is considerably longer than that of commonly used biogenic estrogens. Thus, even though estetrol and estetrol-like substances have relatively low estrogenic potency, they may effectively be administered orally because the oral dosages required to achieve the desired effect are similar to those already used for e.g. 17β-estradiol.

Another important advantage of oral administration of estetrol and estetrol-like substances resides in the fact that the hepatic effects of these substances are deemed to be minimal since they are hardly metabolised during the so called "first pass". The first-pass effect of drugs given orally refers to the process of drug degradation by the liver during a drug's transition from initial ingestion to circulation in the blood stream. After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. Therapeutically equivalent doses of commonly used biogenic estrogens, when applied orally, result in clear responses of hepatic parameters, such as increase of SHBG, CBG and angiotensinogen. These hepatic effects of estrogens are also observed when equine estrogen formulations (so-called conjugated estrogens) are used.

The present method may suitably be used in the (prophylactic) treatment of various estrogen-suppressed tumours, including colorectal tumours and prostate tumours. In the case of treatment or prevention of prostate cancer, the present estrogenic component is suitably administered in an amount effective to inhibit the endogenous production of androgens. The present method is most advantageously employed in the prevention or treatment of colorectal tumours, more preferably in the prevention or treatment of colon tumours.

In a particularly preferred embodiment of the present invention, the method is used to treat a mammal that suffers or has suffered from benign or malign tumours, particularly colorectal tumours. The risk of an estrogen-stimulated cancer is deemed to be particularly high in mammals who have already developed tumours (including adenoma), even if these tumours have been surgically removed or otherwise eliminated. Consequently, the advantages of the present method are particularly pronounced in the treatment of such mammals as treatment with common estrogens would present a significant hazard. The present method is most advantageously employed in the therapeutic treatment of a mammal suffering from estrogen-suppressed tumours.

In a preferred embodiment, the present method comprises the co-administration of a progestogen in an effective amount to suppress endogenous estrogen production. The co-administration of progestogen offers the additional advantage that progestogens are known to inhibit the proliferative effect of estrogens on the endometrium. Although the present estrogenic components, unlike common estrogens, do not appear to have a pronounced proliferative effect on the endometrium, the co-administration of progestogen may be advisable to rule out any potential risks.

Examples of progestogens which may suitably be used in accordance with the present invention include: progesterone, levonorgestrel, norgestimate, norethisterone, dydrogesterone, drospirenone, 3-beta-hydroxydesogestrel, 3-keto desogestrel (=etonogestrel), 17-deacetyl norgestimate, 19-norprogesterone, acetoxypregnenolone, allylestrenol, anagestone, chlormadinone, cyproterone, demegestone, desogestrel, dienogest; dihydrogesterone, dimethisterone, ethisterone, ethynodiol diacetate, flurogestone acetate, gastrinon, gestodene, gestrinone, hydroxymethylprogesterone, hydroxyprogesterone, lynestrenol (=lynoestrenol), medrogestone, medroxyprogesterone, megestrol, melengestrol, nomegestrol, norethindrone (=norethisterone), norethynodrel, norgestrel (includes d-norgestrel and dl-norgestrel), norgestrienone, normethisterone, progesterone, quingestanol, (17alpha)-17-hydroxy-11-methylene-19-nor-pregna-4,15-diene-20-yn-3-one, tibolone, trimegestone, algestone acetophenide, nestorone, promegestone, 17-hydroxyprogesterone esters, 19-nor-17hydroxyprogesterone, 17alpha-ethinyl-testosterone, 17alpha-ethinyl-19-nor-testosterone, d-17beta-acetoxy-13beta-ethyl-17alpha-ethinyl-gon-4-en-3-one oxime and precursors of these compounds that are capable of liberating these progestogens in vivo when used in the present method. Preferably the progestogen used in the present method is selected from the group consisting of progesterone, desogestrel, etonogestrel, gestodene, dienogest, levonorgestrel, norgestimate, norethisterone, drospirenone, trimegestone, dydrogesterone, precursors of these progestogens and mixtures thereof.

In principle, GnRH compositions, as described in U.S. Pat. No. 5,340,584 and U.S. Pat. No. 5,340,585, may also be employed in the present method. Preferably, however, the present method does not employ such a GnRH composition.

Another aspect of the invention relates to a pharmaceutical composition containing:
a. at least 0.05 mg of an estrogenic component as defined herein before;
b. at least 0.01 mg of an anti-tumour component selected from the group consisting of 5α-reductase inhibitors; anti-androgens; cytochrome $P450_{17\alpha}$ inhibitors; α1 adrenoceptor blockers; and microtubule inhibitors; and
c. pharmaceutically acceptable excipient.

The treatment and prophylaxis of estrogen-suppressed tumours with a combination of the present estrogenic component and the aforementioned anti-tumour components is more effective than treatment or prophylaxis with solely the estrogenic component or the anti-tumour component. Such a combination treatment is particularly effective if the anti-tumour component is capable of inhibiting in vivo androgen action, e.g. by inhibiting the biosynthesis of androgens (5α-reductase inhibitors and cytochrome $P450_{17\alpha}$ inhibitors) or by competitive binding to the androgen receptor (anti-androgen).

In a review article by Jarman et al. ("Inhibitors of enzymes of androgen biosynthesis: cytochrome $P450_{17\alpha}$ and 5α-steroid reductase", Nat Prod Rep. 1998 October; 15(5):495-512) it is explained that 5α-reductase inhibitors and cytochrome $P450_{17\alpha}$ inhibitors can be used as potential weapons in the fight against prostatic carcinoma and benign prostatic hypertrophy. The authors observe that about 80% of patients with prostatic cancer have androgen dependent disease and respond to hormonal ablation. Since cytochrome $P^{450}_{17\alpha}$ inhibitors prevent the biosynthesis of the androgen dehydroepiandrosterone, which is a precursor of testosterone and 5α-dihydrotestosterone, and 5α-reductase inhibitors prevent the biosynthesis of 5α-dihydrotestosterone, which androgen is deemed to be particularly harmful, these enzyme inhibitors may be employed advantageously in the treatment of prostatic cancers.

Examples of 5α-reductase inhibitors that may suitably be employed in accordance with the present invention include finasteride, dutasteride (GI-198745), epristeride, turosteride and lipidosterol extract. Abiraterone is an example of a cytochrome $P450_{17\alpha}$ inhibitor that may advantageously be employed in accordance with the invention. Anti-androgens for use in the present method are preferentially selected from the group consisting of cyproterone acetate, osaterone acetate, chlormadinone acetate, flutamide, nilutamide and bicalutamide.

Treatment failure in prostate cancer is usually due to the development of androgen independence and resistance to chemotherapeutic drugs at an advanced stage. Recently, it was reported that α1-adrenoceptor antagonist, such as terazosin, are able to inhibit prostate cancer cell growth. Xu et al. ("The alphal-adrenoceptor antagonist terazosin induces prostate cancer cell death through a p53 and Rb independent pathway", Oncol Rep. 2003 September-October; 10(5):1555-60) report that terazosin inhibits not only prostate cancer cell growth but also colony forming ability, which is the main target of chemotherapy. Examples of α1-adrenoceptor antagonist that can be used in accordance with the invention include terazosin, ABT-980, ABT-627, doxazosin, prazosin, alfuzosin, indoramin and tamsulosin.

Microtubule inhibitors have been proposed as chemotherapeutic agents in the treatment of prostate cancer. Picus and Schultz ("Docetaxel (Taxotere) as monotherapy in the treatment of hormone-refractory prostate cancer: preliminary results", Semin Oncol. 1999 October; 26(5 Suppl 17):14-8) report substantial durable activity for docetaxel as single-agent therapy for hormone refractory prostate cancer. Suitable examples of microtubule inhibitors include taxotere and paclitaxel.

One specific embodiment of the invention is concerned with a drug delivery system comprising a pharmaceutical composition as defined above, said drug delivery system being selected from the group consisting of an oral dosage unit; an injectable fluid; a suppository; a gel; and a cream.

Another specific embodiment relates to a pharmaceutical kit comprising one or more dosage units containing at least 0.05 mg of the estrogenic component as defined herein before and a pharmaceutically acceptable excipient; and one or more dosage units containing at least 0.01 mg of an anti-tumour component selected from the group consisting of 5α-reductase inhibitors; anti-androgens; cytochrome $P450_{17\alpha}$ inhibitors; α1 adrenoceptor blockers; and microtubule inhibitors; and a pharmaceutically acceptable excipient. In a particularly preferred embodiment, the aforementioned dosage units are oral dosage units.

The invention is further illustrated by the following examples:

EXAMPLES

Example 1

A study is performed to examine the effect of estetrol on 1,2 dimethylhydrazine (DMH)-induced colon cancer in ovariectomized female rats.

DMH-induced cancer development is chosen as a model of "estrogen-suppressed tumours", because it mimics the human situation of colon carcinomas closely:
1) tumours grow orthotopically and can be classified as adenocarcinoma with the same histological tests,
2) the route of metastatic formation is the same (tumors grow relatively slowly and progress from adenoma to cancer) and
3) 17beta-estradiol confers protection in the model, as has been previously published (Greene et al., 1987, J. Surgical Research, 43, 476-487; Madara et al., 1983, Am. J. Pathology, 110, 230-235; Smimoff et al., 1999, Oncology Research, 11, 255-264).

One week prior to induction of colon carcinomas, fifty sexually mature female Sprague-Dawley rats, weighing between 150 and 200 gram (Harlan, The Netherlands), are surgically castrated via removal of the ovaries. During the experiment, rats are maintained in separate plastic cages at 12 hour light/dark cycles and allowed free access to food (Purina chow) and water.

Animals are randomly allocated to one of five groups, each consisting of 10 rats, which, starting three days after ovariectomy and ending at autopsy, receive placebo or estetrol treatment during the experiment as follows:
Group 1 animals receiving placebo oral treatment with 3.0 ml/kg/day vehicle (20% wt/vol solution of hydroxypropyl-beta-cyclodextrin in water);
Group 2 animals receiving estetrol orally at a single daily dose of 0.1 mg/kg;
Group 3 animals receiving estetrol orally at a single daily dose of 0.3 mg/kg;

Group 4 animals receiving estetrol orally at a single daily dose of 1.0 mg/kg;

Group 5 animals receiving estetrol orally at a single daily dose of 3.0 mg/kg.

Starting one week after ovariectomy, animals from all groups are given subcutaneously, at weekly intervals, DMH injections (14.7 mg DMH dihydrochloride per 100 gram body weight) for 5 consecutive weeks, using a freshly prepared solution of DMH dihydrochloride in Hank's Balanced Salt Solution.

Fifteen weeks after the first DMH administration, the rats are sacrificed. At necropsy, each animal is incised and the colon is opened and examined closely for any grossly visible tumours before further processing for microscopic analysis. Criteria for determining malignancy are based on examination of histological features of the tumours and observing evidence for tumour invasion into submucosal layers. Only malignant tumours are included in the efficacy analysis.

In rats that have been treated with vehicle only, administration of DMH invariably results in the development of malignant colon tumours. In groups of animals treated with an increasing dose range of estetrol as set forth, the number of malignant tumours declines as a function of increasing the daily oral estetrol dose from 0.1 to 3.0 mg/kg/day.

Example 2

Established competitive steroid binding assays were used to determine the relative binding affinity of estetrol (E4), as compared to 17α-ethinylestradiol (EE) and 17β-estradiol (E2), to human Estrogen Receptor (ER) α- and β-forms.

The method employed was adapted from the scientific literature and described in detail by Osbourn et al. (1993, Biochemistry, 32, 6229-6236). Recombinant human ERα and ERβ proteins were purified from transfected Sf9-cells. The in vitro assays involved the use of either ERα or ERβ proteins and [$^3$H]E2, at a fixed concentration of 0.5 nM, as the labeled ligand. Recombinant human ERα or ERβ proteins were dissolved in binding buffer (10 mM Tris-HCL, pH 7.5, 10% glycerol, 1 mM DTT, 1 mg/ml BSA) and duplicate aliquots were then incubated with [$^3$H]E2 at a final concentration of 0.5 nM, together with a vehicle control (0.4% DMSO), or the same amount of vehicle containing increasing concentrations of unlabeled steroid ligands as competitors. After incubation for 2 h at 25° C., the unbound ligands were removed and the amounts of [$^3$H]E2 bound to either ERα or ERβ proteins were measured. The average amounts of [$^3$H]E2 bound to either ERα or ERβ proteins at each concentration of competitor were used to make inhibition curves. IC50 values were subsequently determined by a non-linear, least squares regression analysis. Inhibition constants (Ki) were calculated using the equation of Cheng and Prusoff (Cheng et al., 1973, Biochem. Pharmacol., 22, 3099-3108), using the measured IC50 of the tested compounds, the concentration of radioligand employed in the assay, and the historical values for the Kd of the radioligand, which were established as 0.2 nM and 0.13 nM for ERα and ERβ, respectively. Biochemical assay results for E4 are presented as the percent inhibition of specific binding in three separate experiments (Table 1). For comparision of binding affinities of E4, EE and E2 to human ERα and ERβ proteins, experimentally observed Ki values are shown in Table 2. As compared to EE and E2, E4 demonstrates a unique binding profile with a strong preference (400%) for binding to the ERα protein (Table 2). In contrast, Ki values for ERβ protein are more pronounced for EE and E2 steroid ligands (Table 2).

TABLE 1

Percent inhibition of specific binding to ERα and ERβ proteins using E4 as unlabeled steroid ligand and 0.5 nM [3H] as labeled competitor. Results of three separate experiments are shown.

| E4 final concentration | ERα steroid binding assay | | | ERβ steroid binding assay | | |
|---|---|---|---|---|---|---|
| | Test 1 | Test 2 | Test 3 | Test 1 | Test 2 | Test 3 |
| 1 μM | 98 | nd | nd | 87 | 90 | 95 |
| 0.3 μM | 92 | 94 | 101 | 74 | 74 | 77 |
| 0.1 μM | 83 | 85 | 86 | 56 | 54 | 50 |
| 0.03 μM | 64 | 66 | 63 | 19 | 25 | 30 |
| 10 nM | 43 | 32 | 28 | nd | nd | nd |
| 3 nM | 26 | 17 | 11 | nd | nd | nd | nd: not determined

TABLE 2

Experimentally determined inhibition constants (Ki) for estetrol (E4), 17α-ethinylestradiol (EE) and 17β-estradiol (E2), to human ERα and ERβ proteins. Relative preference for binding to ERα protein is also shown.

| Steroid ligands | Ki ERα (nM) | Ki ERβ (nM) | Relative ERα/ERβ preference(%) |
|---|---|---|---|
| EE | 0.23 | 0.025 | 11 |
| E2 | 0.21 | 0.015 | 7 |
| E4 | 4.9 | 19 | 400 |

Example 3

In order to further assess the anti-tumour efficacy of the estrogenic substances of the present invention, estetrol was tested in the 7,12-dimethyl-benz(a)anthracene (DMBA)-induced tumour model in rats. This model, originally developed by Huggins et al., 1961 (Nature, 19, 204-207), has been widely used and is a generally accepted model with predictive value for anti-tumour agents in humans. The growth of the DMBA-induced tumours in rats represents an example of "estrogen-stimulated cancers" and is dependent on endogenously produced estradiol or exogenously administered estrogens and prolactin (Sylvester et al., 1982, Cancer Research, 42, 4943-4947). Ovariectomy (Hollingsworth et al., 1998, Breast Cancer Research and Treatment, 47, 63-70), androgens (Dauvois et al., 1989, Breast Cancer Treatment, 14, 299-306), tamoxifen (Hollingsworth et al., 1998, Breast Cancer Research and Treatment, 47, 63-70), progestogens (Kelly et al. 1979, Eur. J. Cancer, 15, 1243-1251; Russo et al., 1987, Lab. Invest. 57, 112-137) and GnRH analogues (Hollingsworth et al., 1998, Breast Cancer Research and Treatment, 47, 63-70) all have been shown to be effective anti-tumour treatments in the DMBA model.

Eighty-four female Sprague-Dawley rats (Harlan, The Netherlands) were group housed, maintained in a 12-hr light/dark environment, and fed a Soya Free Diet (SDS England) and water ad libitum. Animals were weighed on a weekly basis. One week prior to induction of mammary carcinoma, 12 animals (aged 43 days) were surgically castrated via removal of the ovaries. At the age of 50 days, all animals were administered a single oral dose of 16 mg DMBA to induce tumour development. Animals were subsequently allocated to one of seven groups (n=12), receiving placebo or treatment as follows:

Group 1 animals received placebo oral treatment with 3.0 ml/kg/day vehicle (20% wt/vol solution of hydroxypropyl-beta-cyclodextrin in water);

Group 2 surgically castrated animals received placebo treatment with 3.0 ml/kg/day vehicle;

Group 3 animals received the anti-estrogen tamoxifen given orally at a single daily dose of 3 mg/kg;

Group 4 animals received ethinylestradiol (EE) orally at a single daily dose of 0.025 mg/kg;

Group 5 animals received ethinylestradiol (EE) orally at a single daily dose of 0.125 mg/kg;

Group 6 animals received estetrol (E4) orally at a single daily dose of 0.5 mg/kg; and Group 7 animals received estetrol (E4) orally at a single daily dose of 2.5 mg/kg.

The doses of EE and E4 were based on data from previous studies, showing equipotency of 0.025 mg/kg/day EE and 0.5 mg/kg/day E4 in agonistic models of preventing bone resorption, prevention of hot flushing and vaginal cornification. Similarly, the doses of 0.125 mg/kg/day EE and 2.5 mg/kg/day E4 showed equipotency in in vivo estrogenicity in preventing bone resorption, prevention of hot flushing and vaginal cornification.

During the treatment period of 8 weeks, the emergence of palpable tumours and number of tumours were determined weekly. At 8 weeks, at necropsy, final measurements were taken. The number of tumours at necropsy are depicted in FIG. 1. As is clearly demonstrated by the absence of tumours in the ovariectomized animals (group 2), development of DMBA-induced mammary tumours is estrogen-dependent. As expected, also tamoxifen showed anti-tumour properties by inhibiting the development of mammary tumours in this model. Surprisingly, and in contrast to the effect seen with the 0.125 mg/kg/day dose of EE, E4 at an equipotent agonistic dose of 2.5 mg/kg/day markedly suppressed mammary tumour development. Furthermore, this particular dose of E4 was as effective as tamoxifen in preventing growth of DMBA-induced tumours.

The invention claimed is:

1. A method of treating colorectal and/or prostate tumours in a human subject, said method comprising orally administering to the subject at least 0.1 mg per day of an estrogenic component selected from the group consisting of: estetrol, precursors capable of liberating estetrol; and mixtures of estetrol and said precursors;

wherein the precursors capable of liberating estetrol are derivatives of estetrol wherein the hydrogen atom of at least one of the hydroxyl groups of estetrol is substituted by sulfamic acid or sulfonic acid of 1-25 carbon atoms; tetrahydrofuranyl; tetrahydropyranyl; a straight or branched chain glycosidic residue containing 1-20 glycosidic units per residue; or an acyl radical of a hydrocarbon carboxylic.

2. The method according to claim 1, wherein the method comprises uninterrupted administration of the estrogenic component during a period of at least 5 days.

3. The method according to claim 1, wherein the tumours are benign or malignant tumours.

4. The method according to claim 1, wherein the tumours are colorectal tumours.

5. The method according to claim 1, wherein the subject is a female.

6. The method according to claim 1, further comprising co-administering a progestogen.

* * * * *